United States Patent [19]

Goble et al.

[11] Patent Number: 4,927,421
[45] Date of Patent: May 22, 1990

[54] PROCESS OF ENDOSTEAL FIXATION OF A LIGAMENT

[76] Inventors: E. Marlowe Goble, 850 E. 1200 North; W. Karl Somers, 651 N. 150 West, both of, Logan, Utah 84321; David McGuire, 3418 Lakeside Dr., Achorage, Ak. 99515

[21] Appl. No.: 352,153

[22] Filed: May 15, 1989

[51] Int. Cl.$^5$ .............................................. A61F 2/08
[52] U.S. Cl. ....................................... 606/73; 606/96; 623/13
[58] Field of Search ........... 128/92 V, 92 YE, 92 YV, 128/92 YS, 92 YF; 623/13, 20, 16; 606/73, 96, 72, 53

[56] References Cited

U.S. PATENT DOCUMENTS

| | | | |
|---|---|---|---|
| 2,570,465 | 10/1951 | Lundholm | 128/92 YV |
| 4,467,478 | 8/1984 | Jargutis | 623/13 |
| 4,537,185 | 8/1985 | Stednitz | 128/92 YE |
| 4,605,414 | 8/1986 | Czajka | 128/92 YF |
| 4,632,100 | 12/1986 | Somers | 128/92 V |
| 4,668,233 | 5/1987 | Seedhom | 623/13 |
| 4,738,255 | 4/1988 | Goble | 623/13 |
| 4,784,126 | 11/1988 | Hourahane | 128/92 YF |
| 4,790,850 | 12/1988 | Dunn | 623/13 |
| 4,828,562 | 5/1989 | Kenna | 623/20 |
| 4,872,451 | 10/1989 | Moore | 606/73 |

Primary Examiner—Richard J. Johnson
Attorney, Agent, or Firm—M. Reid Russell

[57] ABSTRACT

A cannulated interference screw (10) and process for human implantation in an arthroscopic surgical procedure for replacement of a ligament, or the like. The interference screw is provided with a drill end (11) that extends longitudinally from an end of a cylindrical body (14), which drill end includes equally spaced flutes (12) therearound. The flutes extend into first and second cutting threads (15a) and (15b), respectively which cutting threads and threads (15) are formed around the cylindrical body. A center longitudinal passage (16) is formed through the interference screw drill end and cylindrical body, which passage is stepped outwardly within the cylindrical body into a hexagonal sided section (18) that is for receiving a sided end (20) of a driver (19) that is fitted therein. In practice, the cannulated interference screw is installed by sliding it along a guide rod (25) that is fitted in a prepared ligament tunnel (22) through a bone mass, alongside a bone block portion of a ligament (23) within the bone endosteum, which ligament is maintained in that tunnel under tension. The driver is also holed longitudinally to travel along the guide rod to fit into and turn the interference screw, providing fixation of the ligament in that tunnel.

4 Claims, 2 Drawing Sheets

PROCESS OF ENDOSTEAL FIXATION OF A LIGAMENT

BACKGROUND OF THE INVENTION

1. Field of the Invention

This invention relates to fixation devices and more particularly to arrangements for anchoring a ligament in a bone mass.

2. Prior Art

Until recently, in ligament repair and/or replacement surgery involving securing of one or both ligament ends to a bone mass have been accomplished utilizing staples, or like fixation devices, that are driven through or across the ligament and into the bone mass. Such ligament anchoring has involved connecting the ligament end to the bone mass exterior, requiring, for a knee cruciate ligament procedure, that the replacement ligament end or ends extend onto the periosteum or outside bone surface beyond a ligament tunnel with each end bent and secured onto the bone mass surface. Such ligament bending, of course, may result in a force concentration at that bend, weakening and potentially subjecting the ligament to rupture.

An earlier patent issued to two of the present inventors in a "Suture Anchor Assembly", U.S. Pat. No. 4,632,100, addresses anchoring a suture to a bone mass surface for joining a ligament thereto, but does not address securing a ligament in a ligament tunnel, as does the present invention. Another patent issued to two of the present inventors in a "Ligament Attachment Method and Apparatus", U.S. Pat. No. 4,772,286 does involve an endosteal fixation device for securing, at a certain tension, a ligament in a ligament tunnel. End coupling arrangements including a threaded flattened cone, expanding cone, and threaded cylindrical end anchors, that are taught by this patent, however, are structurally and functionally unlike the present invention. Also, still another invention of two of the present inventors in a "Ligament Anchor System", filed as a U.S. patent application, Ser. No. 289,728 is also an endosteal fixation system that includes a sleeve for turning in a tapped cortex, the sleeve to receive a footing turned therein that mounts a ligament. None of the inventions set out in these patents or in the patents cited therein or as were cited during the individual applications prosecutions, however, involve wedging a ligament bone block portion in a ligament tunnel as taught by the present invention.

The interference screw of the present invention is similar in construction to the anchor shown and described in the above-cited U.S. Pat. No. 4,632,100 of two of the present applicants, in that both involve a threaded cylindrical body with a forward fluted drill end. The patented anchor, of course, is for turning into a bone mass, whereas the interference screw of the present invention is cannulated for guided travel on a guide wire by a driver into a ligament tunnel, alongside a ligament fitted therein. The interference screw of the present invention is principally for wedging between a bone block portion of a ligament and tunnel wall, and is accordingly both structurally and functionally unlike the patented anchor.

BRIEF SUMMARY OF THE INVENTION

It is therefore a principal object of the present invention in an interference screw and system to provide a device for endosteal fixation or the surface of a bone block portion of a ligament and the wall of a ligament tunnel formed through a bone mass.

Another object of the present invention is to provide a cannulated interference screw having a drill end for both drilling a hole into a bone mass followed by the interference screw threads, which threads have at least one leading thread for cutting into that drilled hole.

Another object of the present invention is to provide an arrangement for guiding the cannulated interference screw between a ligament tunnel wall and the bone block portion of a ligament installed therein.

Still another object of the present invention is to provide a driver and guide wire for precisely and conveniently turning the interference screw between a ligament tunnel wall and the bone block surface of a ligament fitted therein, the driver and guide wire also providing an arrangement for conveniently removing the interference screw.

Still another object of the present invention is to provide a simple and reliable device and system for fixing a bone block portion of a ligament within a ligament tunnel that is formed through a bone mass.

In accordance with the above objects, the present invention is in an interference screw and a system for its use to provide for securing a bone block portion of one or both ligament ends under tension within a prepared ligament tunnel that has been passed through a bone mass. In practice, a ligament tunnel, as for example, an anterior or posterior cruciate ligament tunnel is prepared in the distal femur and proximal tibia portions of a patient's knee in an arthroscopic surgical procedure. In that procedure a surgeon monitors drilling progress on a fluoroscopic monitor, or the like. The procedure involves both preparing the tunnel through both the distal femur and proximal tibia bone ends and installing either an allograft or prosthetic ligament, in that prepared tunnel. Wherein, that ligament is maintained under tension.

The interference screw of the present invention is to secure a bone block portion of the ligament end or ends in the tunnel. The interference screw preferably includes a cylindrical body with a fluted drill on a forward end and is threaded from that fluted drill to a rear end. The flutes of the drill are cut into the adjacent threads to provide self-tapping sharp cutting edges, that follow the fluted drill into a bone mass. Also, the interference screw is cannulated, having a center longitudinal passage therethrough that is sided on a rear end opposite to the fluted drill end to receive a driver fitted therein.

The cannulated interference screw and driver are to slide and turn along a guide wire that is fitted into the ligament tunnel, alongside the bone block portion of the ligament positioned therein. The driver turns the interference screw along the ligament tunnel wall and ligament surface, as viewed on the fluoroscopic monitor, to where the interference screw is appropriately positioned so as to provide an interference fit therebetween. Whereat, the driver and guide pin are removed.

The cannulated interference screw is removed by reinserting the guide pin with the driver telescoped thereon along the ligament tunnel and into the interference screw longitudinal cavity, the driver to fit into the interference screw for turning it out of the ligament tunnel.

DESCRIPTION OF THE DRAWINGS

In the drawings that illustrate that which is presently regarded as the best mode for carrying out the invention.

DETAILED DESCRIPTION

Figure 1:
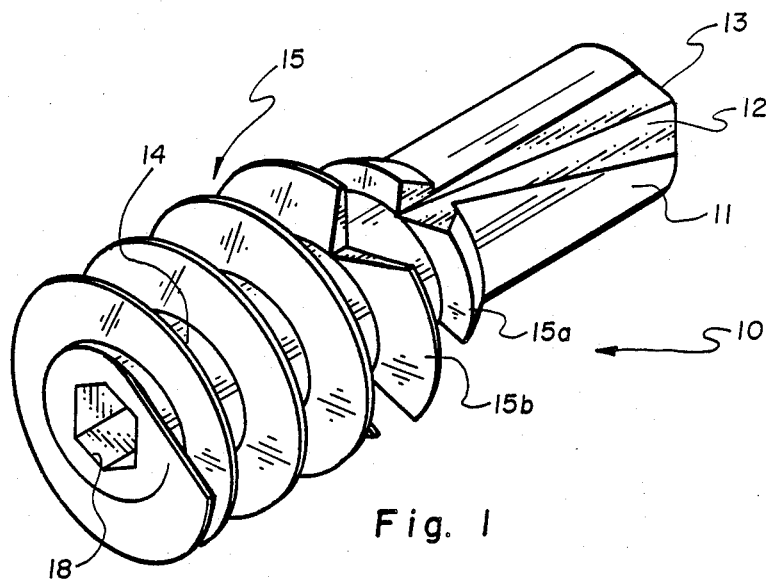
FIG. 1 is a profile perspective view of the present invention in a cannulated interference screw.
Figure 2:
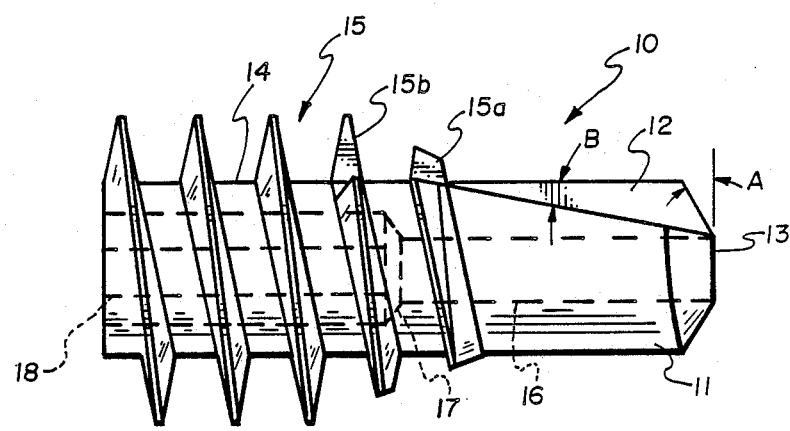
FIG. 2 is a side elevation view of the cannulated interference screw of FIG. 1 showing, in broken lines, that a longitudinal passage therethrough is stepped outwardly into a sided rear end cavity.
Figure 3:
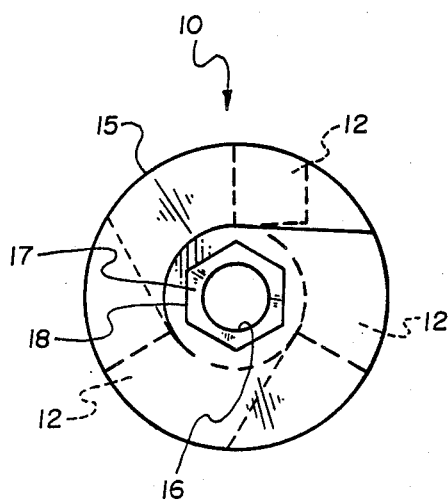
FIG. 3 is a rear end elevation view of the cannulated interference screw of FIG. 1.
Figure 4:
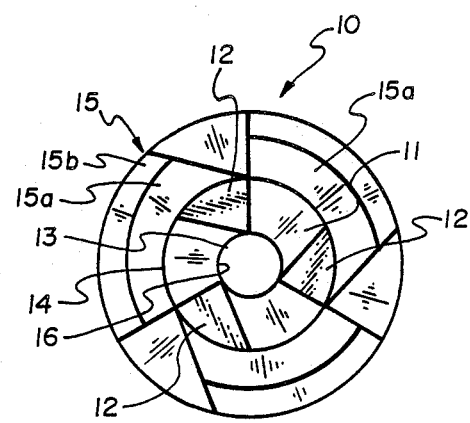
FIG. 4 is a forward end elevation view of the cannulated interference screw of FIG. 1.

FIG. 1 shows a preferred embodiment of a cannulated interference screw 10 of the present invention, hereinafter referred to as screw. The screw 10, as shown best in FIGS. 1 through 4, includes a drill 11 that extends longitudinally from its forward end that preferably incorporates three (3) longitudinal flutes 12 arranged at one hundred twenty (120) degree intervals around the drill. The flutes 12 extend from a drill forward or nose end 13 that, as shown at A in FIG. 2, is angled rearwardly at approximately a thirty (30) degree angle to the vertical. Each flute tapers outwardly along the drill 11, as shown at B in FIG. 2, at approximately a ten (10) degree angle from the horizontal. The flute walls are shown to taper together passing into forward cutting threads 15a and 15b of threads 15.

Threads 15 are formed around a cylindrical screw body 14. Shown best in FIGS. 1, 2, and 4, the flutes 12 are shown to be spaced at one hundred twenty (120) degree intervals from drill nose end 13 to pass through first and second cutting threads 15a and 15b, respectively. The cutting thread 15a is shown to have a lesser outside diameter than that of cutting thread 15b, and the other threads 15. The intersection walls of the cutting threads 15a and 15b at flutes 12 from walls that are preferably angled at approximately right angles to the vertical axis of the thread as cutting edges. Thereby, in turning the screw 10 into a bone mass, the drill 11 will form a hole and travel into that bone mass to where the first cutting thread 15a, at its intersection to one of the drill flutes 12 will contact and cut into that bone mass. The second cutting thread 15b follows the first to further deepen the cut thread to receive the following individual threads of threads 15 turned therein. Accordingly, the arrangement of drill 11 and threads 15 provide a single device for drilling, tapping and seating in a bone mass. Also, while, as shown best in FIG. 2, the threads are preferably tapered, they need not be within the scope of this disclosure.

Figure 6:
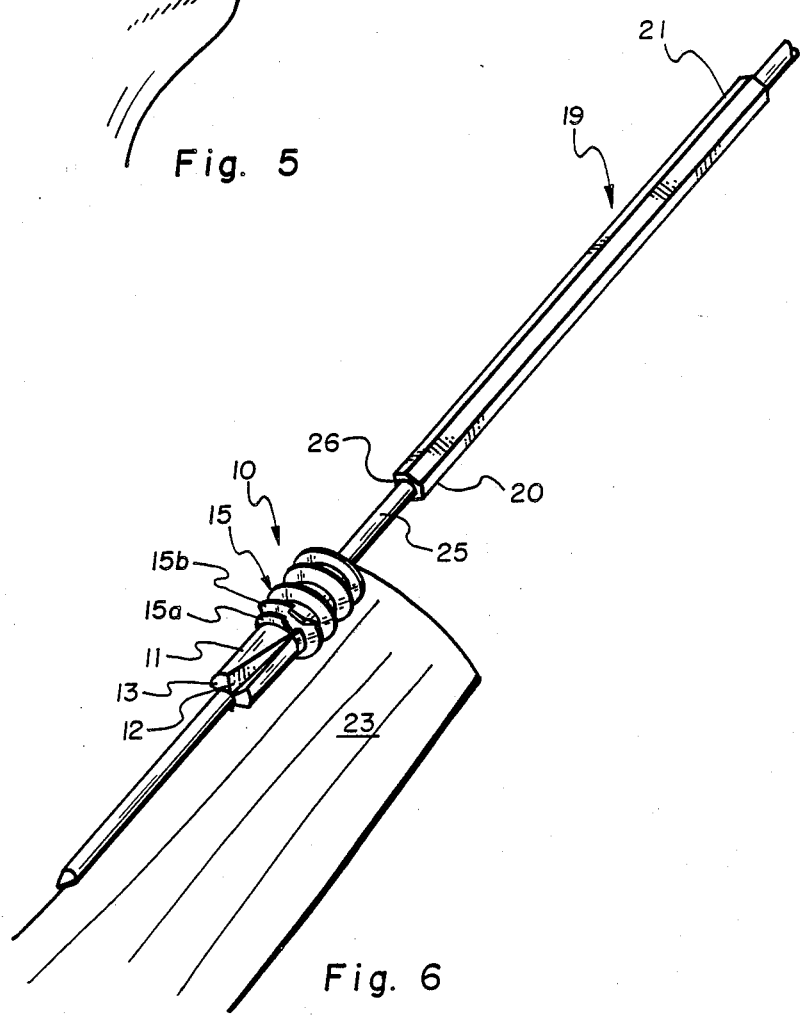
FIG. 6 is a view of a section of the bone block portion of the ligament and cannulated interference screw with guide rod of FIG. 5, and showing a driver that is telescoped over the guide rod that has a sided end for fitting into the sided end of the cannulated interference screw end.

Shown in broken lines in FIG. 2, the drill 11 and screw body 14 include a center longitudinal passage 16 therethrough that is preferably stepped outwardly at 17 into a sided rear section 18. The sided rear section 18 walls are preferably hexagonal to receive, as shown in FIG. 6, a hexagonal shaped end 20 of a driver 19 that is fitted therein for turning screw 10. Which driver opposite end 21 is arranged to receive a chuck of a tool, not shown, that is either manually or motor driven for turning the driver, as set out below.

Figure 5:
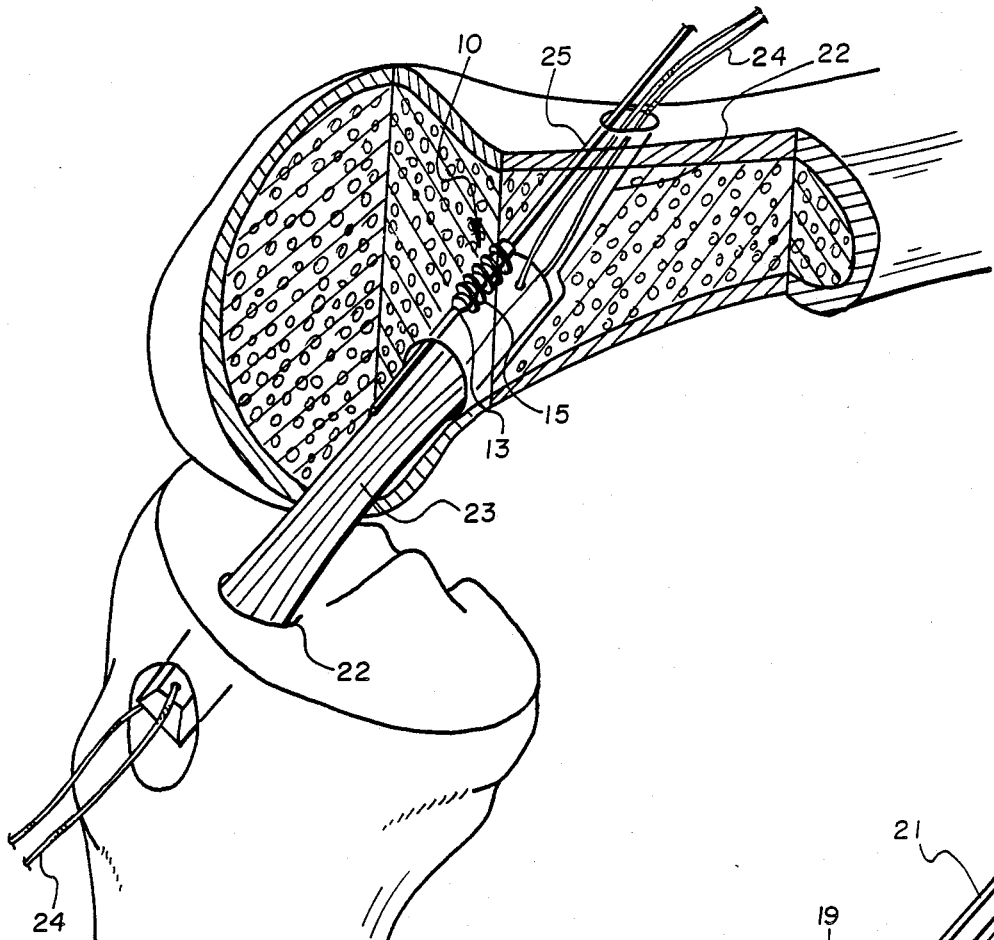
FIG. 5 is a profile perspective view of a patient's knee with a portion of the distal femur shown broken away that includes a ligament tunnel formed through the knee and showing an anterior cruciate ligament maintained in tension therein, the cannulated interference screw of FIG. 1, shown fitted to slide along a guide rod that is passed from the femur cortex ligament tunnel end, traveling alongside a bone block portion of the ligament.

FIG. 5 shows a patient's knee with a portion of the distal femur cut away, exposing an anterior cruciate ligament tunnel 22, hereinafter referred to as ligament tunnel, that is formed therein, and extends across the knee through both the distal femur and proximal tibia. The ligament tunnel is shown to open at the tibial tuberosity and anterolateral femoral cortex ends of that ligament tunnel. The ligament tunnel 22 is preferably formed by conventional surgical procedures, such as, for example, the procedure set out in the patent of two of the applicants, U.S. Pat. No. 4,772,286, or by like procedure, within the scope of this disclosure.

As shown in FIG. 5, a ligament 23, that can be a prosthetic or allograft ligament, or the like, is fitted into the ligament tunnel 22. Sutures 24 are shown connected to the ligament ends that extend out from the ligament tunnel ends and are for use in applying a tensile force on the ligament. So arranged, to install the screw 10 for providing an interference fit between the ligament tunnel 22 wall and a bone block side portion of ligament 23, a surgeon, observing on a fluoroscopic monitor, or the like, fits a guide rod 25 through an end of the ligament tunnel 22, sliding it along the bone block portion of the ligament.

With the guide rod 25 installed as shown in FIG. 5, a surgeon can fit or telescope the longitudinal passage 16 of screw 10 onto the guide rod 25. A center passage 26 of the driver 19 is then fitted or telescoped onto that guide rod, and passed therealong until the driver sided end 20 fits into the sided end 18 of the screw longitudinal passage 16. The driver 19 is then mounted to the drill 11 end 13 for turning into and between the ligament tunnel 22 and ligament 23 providing an endosteum or endosteal fixation therebetween. In that turning, the screw 10 travels to the attitude shown in FIGS. 5 and 6. Whereat, the guide rod 25 can be pulled out of the screw and ligament tunnel providing an endosteum or endosteal fixation, the screw installed therein prohibiting the bone block portion of the ligament 23 from being pulled out of that ligament tunnel 22. In practice, the screw 10, installed as shown in FIG. 5, has prohibited a bone block portion of the ligament 23 from removal from ligament tunnel 22 to an applied tensile force of approximately one hundred fifty (150) pounds. Which force is well above a maximum anticipated tensile stress in running of approximately eighty (80) pounds.

It should be understood that the installation of the screw 10 in the proximal tibia portion of the ligament tunnel 22 is like that described above for screw installation in the distal femur portion of that ligament tunnel. Also, as desired, within the scope of this disclosure, more than one screw per tibial and femoral endosteum ligament tunnel sections can be used for increasing ligament holding strength, as desired and, rather than fitting the screw into the ligament tunnel, alongside the bone block portion of the ligament, a hole can be drilled across that ligament tunnel, through the bone block portion and the screw turned therethrough.

The screw 10 is preferably manufactured from a material that is suitable for sterilization and human implantation and, in practice, the preferred screw is manufactured from a titanium or type 316 stainless steel. It should, however, be understood, screw 10 can be manufactured from any material that is suitable for human implantation, to include a bio-degradable material such as a bio-erodible plastic, or the like, providing such a biodegradable material is sufficiently hard to provide the described functions.

While a preferred embodiment of the invention in an interference screw and its use has been shown and described herein, it should be apparent that this disclosure is made by way of example only and that variations to the invention are possible within the scope of this disclosure without departing from the subject matter coming within the scope of the following claims and a reasonable equivalency thereof, which claims we regard as our invention.

We claim:

1. A process of endosteal fixation of a ligament within the interior of a bone mass comprising, forming a ligament tunnel through adjacent bone masses; fitting a ligament under tension in said ligament tunnel, extending between said adjacent bone masses; and turning a threaded device into one end of said ligament tunnel, guiding it alongside the ligament, such that the threads of said threaded device turn into said tunnel wall and a bone block end portion of said ligament.

2. A process of endosteal fixation as recited in claim 1, wherein the threaded device is cannulated and is arranged for travel and turning along a guide wire that is fitted into the ligament tunnel, alongside the ligament.

3. A process of endosteal fixation as recited in claim 1, wherein the threaded device has a threaded body and includes a drill extending from one or a first end with an arrangement for fitting a driver formed in the other or second end.

4. A process of endosteal fixation as recited in claim 3, wherein the threaded device and driver are both cannulated to travel along a guide wire that is for fitting into the ligament tunnel, alongside the bone block end portion of the ligament.

* * * * *